US011098276B2

(12) United States Patent
Emminger et al.

(10) Patent No.: US 11,098,276 B2
(45) Date of Patent: Aug. 24, 2021

(54) PHOTOBIOREACTOR HAVING MOVABLE MAINTENANCE DEVICE

(71) Applicant: Beco Invest B.V., Houten (NL)

(72) Inventors: Franz Emminger, Hainburg (AT); Silvia Fluch, Weiden/See (AT)

(73) Assignee: Beco Invest B.V., Houten (NL)

(*) Notice: Subject to any disclaimer, the term of this patent is extended or adjusted under 35 U.S.C. 154(b) by 252 days.

(21) Appl. No.: 16/329,053

(22) PCT Filed: Aug. 30, 2017

(86) PCT No.: PCT/EP2017/071702
§ 371 (c)(1),
(2) Date: Feb. 27, 2019

(87) PCT Pub. No.: WO2018/041859
PCT Pub. Date: Mar. 8, 2018

(65) Prior Publication Data
US 2019/0218491 A1 Jul. 18, 2019

(30) Foreign Application Priority Data

Aug. 30, 2016 (EP) .................................... 16186440
Feb. 8, 2017 (EP) .................................... 17155258

(51) Int. Cl.
C12M 1/00 (2006.01)
C12M 1/12 (2006.01)
C12N 1/12 (2006.01)

(52) U.S. Cl.
CPC ............ C12M 21/02 (2013.01); C12M 23/06 (2013.01); C12M 23/34 (2013.01); C12M 29/06 (2013.01); C12M 39/00 (2013.01); C12N 1/12 (2013.01)

(58) Field of Classification Search
CPC .................................................... C12M 39/00
See application file for complete search history.

(56) References Cited

U.S. PATENT DOCUMENTS

2011/0027875 A1 2/2011 Cathcart
2014/0242681 A1 8/2014 Fiorentino
2017/0130181 A1 5/2017 Emminger

FOREIGN PATENT DOCUMENTS

CN 202 968 549 6/2013
DE 102009029792 A1 12/2010
(Continued)

OTHER PUBLICATIONS

Int'l Search Report (Form PCT/ISA/210) conducted in Int'l Appln. No. PCT/EP2017/071702 (dated Nov. 27, 2017).
(Continued)

Primary Examiner — Rosanne Kosson
(74) Attorney, Agent, or Firm — Maier & Maier, PLLC

(57) ABSTRACT

The present invention relates to a photobioreactor 1 for cultivating phototrophic microorganisms, comprising a reactor element 2, which has a tube 3, a maintenance device 4, and a drive system 5, which can move the maintenance device 4 in the tube 3. The photobioreactor is designed such that liquid culture medium 6 containing the microorganisms flows through at least some of the tube 3 when the photobioreactor 1 is in the operating state. The invention is characterised in that the photobioreactor 1 is designed such that the maintenance device 4 can be used in the tube 3 when the photobioreactor 1 is in operating state and can be moved in the tube 3 at least counter to the flow of the culture medium 6 by the drive system 5. The invention also provides a method for cultivating phototrophic microorganisms in a photobioreactor having a movable maintenance device, a movable maintenance device for maintaining the inner surface of a tube of a photobioreactor for cultivating phototrophic microorganisms, and the use thereof during operation of the photobioreactor.

14 Claims, 11 Drawing Sheets

(56) References Cited

FOREIGN PATENT DOCUMENTS

| EP | 1 632 562 | 3/2006 |
| --- | --- | --- |
| EP | 2 947 139 | 11/2015 |
| WO | 94/09112 | 4/1994 |
| WO | 2009/051478 | 4/2009 |
| WO | 2010/025345 | 3/2010 |
| WO | 2011015653 A2 | 2/2011 |
| WO | 2014/133793 | 9/2014 |
| WO | 2015/179888 | 12/2015 |
| WO | 2016/168871 | 10/2016 |

OTHER PUBLICATIONS

Int'l Written Opinion (Form PCT/ISA/237) conducted in Int'l Appln. No. PCT/EP2017/071702 (dated Nov. 27, 2017).

Europe Search Report and Office Action conducted in counterpart Europe Appln. No. 16186440.0 (dated Feb. 20, 2017) (w/ machine translation).

Europe Search Report and Office Action conducted in counterpart Europe Appln. No. 17155258.1 (dated Jul. 27, 2017) (w/ machine translation).

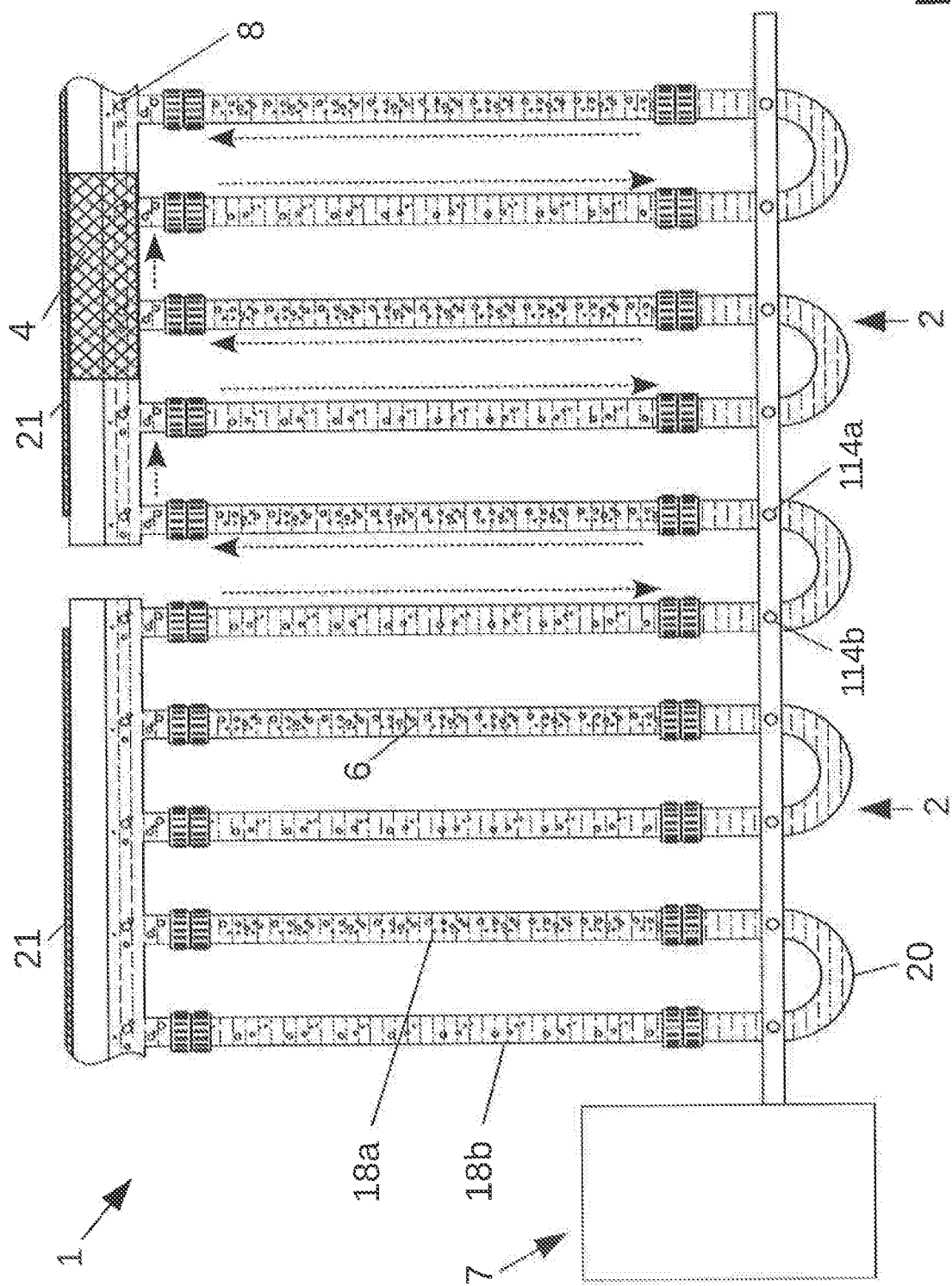

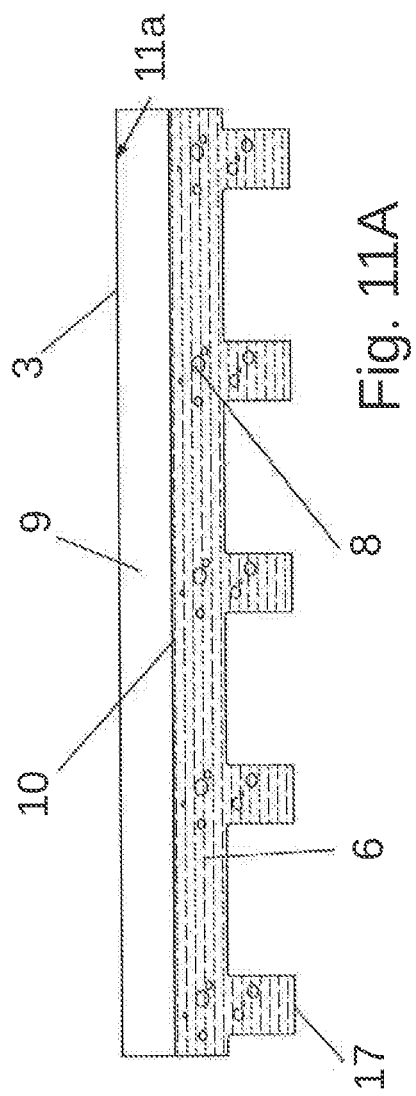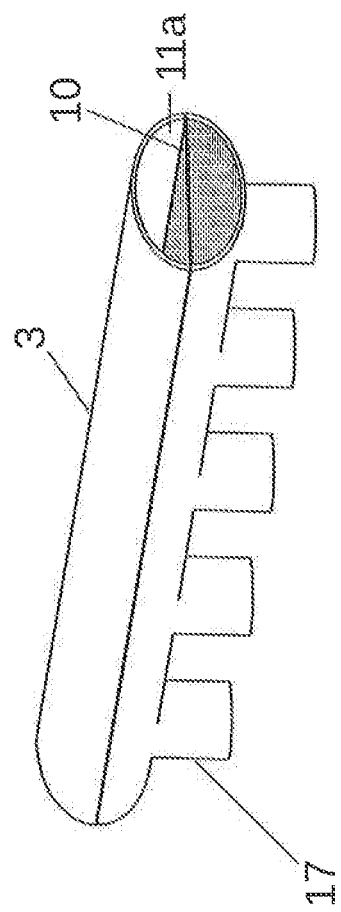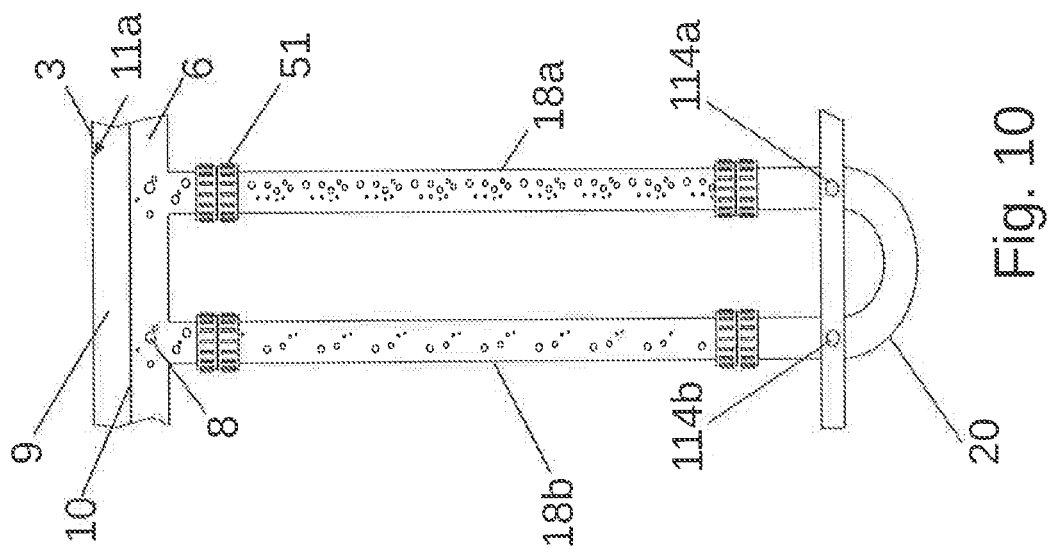

PHOTOBIOREACTOR HAVING MOVABLE MAINTENANCE DEVICE

The field of the present invention is that of tubular photobioreactors for the cultivation of phototrophic microorganisms such as microalgae, wherein the tubular photobioreactors are equipped with a tube maintenance device.

Phototrophic microorganisms such as microalgae are mainly cultivated because of their valuable ingredients, which are needed, for example, in the production of medical preparations, food and feed, dietary supplements, and cosmetics. These ingredients include, among others, unsaturated fatty acids (for example, omega-3 and omega-6 fatty acids), antioxidants such as astaxanthin and lutein, and chlorophyll. The composition of the ingredients depends on the cultivated nature of phototrophic microorganisms. A pure culture of phototrophic microorganisms is predominantly used to be able to ensure a certain quality or minimum concentration of the desired ingredients.

Usually, the microorganisms operating the photosynthesis are cultivated under the action of light (for example, sunlight) in the nutrient-containing culture medium in a photobioreactor, and then concentrated and processed. The ingredients can be extracted from the biomass obtained for further processing or the biomass itself can be used, for example, as feed or fertilizer. For example, WO 2015/179088 A1 discloses a photobioreactor or WO 2016/168871 A2 or CN 202 968 549 U discloses a harvesting device for algae.

In general, the tubes of a photobioreactor, in particular in continuous operation, are susceptible to contamination over time. Often in this case, residues from cultivation (for example, from remnants of dead microorganisms) accumulate on the inside of the tubes. This can, on the one hand, reduce the luminous efficacy (since these residues typically absorb light) and, on the other hand, represent a constant danger with regard to contamination of the culture medium with unwanted microorganisms, which find a suitable nutrient medium in the residues. In turn, the yield from the cultivation can be significantly reduced due to reduced luminous efficacy or contamination. Furthermore, it may be of great importance for product safety, in particular for sensitive domains such as the production of medical preparations or food supplements, to exclude as much as possible contamination of the culture with unwanted microorganisms.

The prior art proposes different solutions to the problem explained above.

WO 94/09112 A1 discloses a device for cleaning photobioreactor tubes and a photobioreactor which comprises the same device. Essentially, this device moves mobile cleaning elements (for example, balls rubbing against the inner surface of the tube) with a magnetic core, which in turn drives the culture medium through a "piston effect". As a result, according to the document, pumps or generation of a flow by "gas lift" can be dispensed with.

EP 2 947 139 A1 relates to a reactor for the photochemical cultivation of a liquid culture of small organisms and microbes, in particular algae, a cleaning method for this and its use. In this case, substantially for cleaning by the pump of the reactor, skids, each having a cleaning part, are moved along the flow direction in the tubes of the reactor.

WO 2010/025345 A2 relates to a "semi-closed loop" photobioreactor for the production of diesel fuel from algae using wastewater. A cleaning device, which may be formed, for example, as a cleaning brush device, is disclosed therein, which has a magnetic core and can be moved by a magnet located outside of the photobioreactor tube (see FIG. 8 of the document). The document teaches in paragraph [0041] that the photobioreactor is rinsed and cleaned after the harvest of the algae (that is, between the operating cycles in which algae are cultivated).

WO 2014/133793 A1 relates to a modular tubular bioreactor. Disclosed herein is a cleaning module that may comprise a pig, scrubber, or cleaning beads that may circulate with the flowing culture medium.

EP 1 632 562 A2 relates substantially to a tubular photobioreactor halving a meandering flow path, between the tubes of which connecting pieces are provided, in the inner region of which cleaning slides are arranged. According to one embodiment, the cleaning slide can be pushed through an inspection opening with a plug-in push rod into the tube.

Despite these proposed solutions, there is a need for further developments that, for example, increase the scalability and lifetime of photobioreactors.

It is the object of the present invention to further improve the interaction between the photobioreactor and the maintenance device (which may, for example, have a cleaning function) or to further improve the photobioreactor or the maintenance device itself, so that the service life and/or yield of the photobioreactor is increased or the maintenance effort is reduced.

Therefore, the present invention provides a photobioreactor for cultivating phototrophic microorganisms, having a reactor element which comprises a tube, and further having a maintenance device and a (preferably external) drive system that can move the maintenance device in the tube. The photobioreactor is designed such that liquid culture medium having the microorganisms at least partially flows through the tube in the operating state of the photobioreactor. In addition, the photobioreactor according to the invention is designed such that the maintenance device can be used in the operating state of the photobioreactor in the tube and can be moved by the drive system at least against the flow of the culture medium in the tube. The stated object is achieved as a result.

Accordingly, the invention also provides a method of cultivating phototrophic microorganisms in a photobioreactor. This photobioreactor is equipped with a reactor element which comprises a tube, and with a maintenance device in the tube and with a drive system which moves the maintenance device in the tube, wherein liquid culture medium having the microorganisms at least partially flows through the tube. According to the invention, the method is characterized in that it comprises the use of the maintenance device in the tube in the operating state of the photobioreactor, preferably while the culture medium is exposed to sunlight or artificial light, and the maintenance device is moved by the drive system at least against the flow of the culture medium in the tube. This also solves the stated problem.

Unlike proposals known in the prior art for maintaining a photobioreactor, according to which, for example, cleaning beads are to circulate with the flow in the photobioreactor (that is, "passive") to keep the reactor walls clean, the present invention proposes, as described above, a movement of the maintenance device at least against the flow of the culture medium, usually along the longitudinal axis of the tube in the operating state of the photobioreactor (expediently, the maintenance device can also be moved by the drive system in the direction of the flow of the culture medium, visually along the longitudinal axis of the tube). Thus, positions in the tube (for example, having contaminants that must be removed urgently) can be reached independently of the flow (that is, without requiring circulation through the entire photobioreactor, so that positions can be reached more quickly). Contamination-related shutdowns are thus ultimately avoided and the yield of the photobioreactor is increased.

Also, the maintenance device itself is usually affected by contamination (for example, residues of dead microorganisms may be deposited on surfaces of the maintenance device). Conventionally, therefore, a maintenance device must be removed from the photobioreactor in order to clean it. In the course of the present invention, however, it has proven to be particularly advantageous when the photobioreactor further comprises a device for gassing the culture medium, wherein the photobioreactor is designed such that in the operating state of the photobioreactor, the maintenance device is brought into contact with gas bubbles present in the (gassed) culture medium in the tube. The gas bubbles gradually rising in the culture medium due to their buoyancy slow at prevent the build-up of residues on surfaces of the maintenance device, whereby the frequency of removal of the maintenance device from the photobioreactor for its cleaning can be reduced.

The photobioreactor according to the invention is designed in a preferred embodiment such that both culture medium and, above the culture medium, a gas space for receiving gas bubbles rising from the culture medium, are present in the operating state in the tube, wherein an interface is arranged between the culture medium and the gas space in the tube. However, during the development of this embodiment, it has been found that it is precisely the inner surfaces of the tube (or the "interface space" in the immediate vicinity of the interface) which are in contact with the interface between the culture medium and the gas space, which are susceptible to contamination, wherein generally more and more contamination accumulates with the duration of operation. In the region of the interface (which often varies slightly in height over the period of operation), foaming and deposition of residues of the phototrophic microorganisms can occur again and again. In addition, it sometimes happens that the inner surface of the photobioreactor is spattered with culture medium and these spatters also dry over time and thereby form contaminants. Therefore, in this embodiment, the maintenance device is set up at least for cleaning inner surface of the tube which inner surface is in contact with the gas space (that, is, for the particularly susceptible regions of the tube). Expediently, the gas space in the tube formed as a manifold (which gas space is located above the culture medium in the manifold) is preferably a gas space which extends along the longitudinal axis of the manifold over at least 10%, preferably at least 20% or even at least 30%, more preferably at least 40% or even at least 50%, even more preferably at least 60% or even at least 70%, in particular at least 80% or even at least 90% of the length of the manifold. It is particularly expedient when said gas space extends over the entire length of the manifold. Naturally, the term "gas" can also be understood to mean a gas mixture, in particular a mixture of a gas (for example, carbon dioxide) with air.

Advantageously, the maintenance device of the photobioreactor according to the invention comprises a spray nozzle for spraying the inner surface of the tube with a cleaning liquid. This has proven as gentler and more hygienic compared to a brushing equipment in continuous operation. In this case, it is particularly preferred when the maintenance device is set up at least for spraying the inner surface of the tube which inner surface is in contact with said gas space by the spray nozzle. In this way, deposits (which can arise over time as described above) can be better eliminated.

In a further preferred embodiment, the maintenance device comprises at least one wiper blade made of an elastic material, such as a rubber, for wiping the inner surface of the tube. This has also proven as gentler and more hygienic compared to a brushing equipment in continuous operation. In this case, it is particularly preferred when the maintenance device is set up at least for wiping the inner surface of the tube with the wiper blade which inner surface is in contact wish said gas space. In this way, existing contamination (which can arise over time as described above) can be better eliminated. Alternatively, or additionally, the maintenance device preferably comprises a, possibly further, spray nozzle, which is set up to spray the wiper blade with a cleaning liquid. This reduces the risk of residues forming on the wiper blade.

When said spray nozzle is fed with culture medium located in the tube (which contains the phototrophic microorganisms), the microorganisms are also usually sprayed with it, whereby they are exposed to high shear forces. This can lead to the death of microorganisms (in particular some species of algae are highly sensitive to shear forces) and thus reduce the yield. Due to this, in a preferred embodiment, the spray nozzle is connected via a line (for example, via a water line) to a liquid reservoir outside the tube. This liquid reservoir preferably contains a germ-reduced or sterile cleaning liquid (of course, not said culture medium with microorganisms), such as sterile, filtered water.

According to a further, particularly preferred embodiment of the present invention, in the operating state of the photobioreactor, the maintenance device in the tube can be flowed around, and/or flowed through by the culture medium (for example, by being in the form of a hollow cylinder). As a result, the continuous operation of the photobioreactor can be better ensured (even with a longer residence time in the tube). Preferably, the maintenance device blocks at most 97.5%, preferably at most 95%, more preferably at most 92.5% or even at most 90%, even more preferably at most 87.5% or even at most 85%, in particular at most 82.5% or even at most 80% of the cross-sectional area of the tube at the location in the tube most heavily blocked by the maintenance equipment.

The maintenance device is designed in an advantageous development such that, while it is located in the tube, which has a first diameter, can clean with a cleaning instrument releasable from the maintenance device (see FIG. 3) a further tube connected to the tube in a liquid-permeable manner at an angle (preferably between 40° and 140°, more preferably between 60° and 120°, more preferably between 80° and 100°, in particular substantially 90°), which further tube optionally has a diameter smaller or larger, preferably smaller, to the first diameter, optionally at the same time as the cleaning of the former tube. In this way, the same maintenance device can be used for tubes of different diameters connected with each other.

In a further preferred embodiment of the photobioreactor, the tube is a manifold having at least three connections for the inflow or outflow of culture medium. The photobioreactor in this embodiment is designed such that the maintenance device can be moved to at least one of the connections in the tube and can seal the connection. Thus, without disturbing the running operation (while the culture medium continues to flow in the tube), maintenance work can be performed beyond the sealed connection. The aforementioned connections can be formed, for example, as bores, openings or connection extensions.

It is favorable when the tube (in particular when it is formed as a manifold), along its longitudinal axis, does not comprise a slope or rise at an angle (with respect to the level of the culture medium) of greater than 10°, preferably of greater than 5°, more preferably greater than 2.5°, even more preferably greater than 1° or even greater than 0.5°. Particularly preferably, the manifold (along its longitudinal axis) is oriented substantially horizontally or horizontally (that is, its longitudinal axis is substantially parallel or parallel to the level of the culture medium).

Of particular advantage is said sealing function, when the reactor element further comprises a plurality of risers (rising pipes) and down pipes for the liquid culture medium, wherein the risers and down pipes are each connected in a liquid-permeable manner at their upper end to the tube formed as a manifold, wherein at least one of the risers and one of the down pipes are additionally connected in a liquid-permeable manner to each other by a connecting piece. In this case, the photobioreactor is designed such that the maintenance device can, at the same time, seal the connection for the down pipe and the connection for the riser, which are both connected to each other in a liquid permeable manner additionally by a connecting piece (that is, can form a so-called "U-tube"). The riser or the down pipe or the connecting piece can thereby be replaced without disturbing the current operation. Usually, only the culture medium located in the riser and down pipe (or in the connecting piece) has to be drained off beforehand.

A connecting piece preferably connects exactly one of the risers with exactly one of the down pipes in a liquid-permeable manner (or connect the two to each other in a liquid-permeable manner). It is preferred in this case that at least all except one or two risers of the reactor element and/or at least all except one or two down pipes of the reactor element are each pairwise connected in a liquid-permeable manner with such a connecting piece, in particular at least all except one riser of the reactor element and/or at least all except one down pipe of the reactor element are each pairwise connected to such a connecting piece in a liquid-permeable manner. It is structurally favorable (in particular to support a meandering flow) when a connecting piece connects a riser and a down pipe that are adjacent to each other (that is, are adjacently connected to the manifold) to each other in a liquid-permeable manner.

According to the invention, said plurality of risers or down pipes of the reactor element, which are connected in a liquid-permeable manner to the same tube formed as a manifold, is at least three (for example, in the arrangement down pipe-riser-down pipe or riser-down pipe-riser along the manifold). It is favorable in terms of scalability of the cleaning, when said plurality is at least four, preferably at least five, more preferably at least ten, even more preferably at least twenty, in particular at least thirty or even at least forty or at least fifty or at least one hundred. Advantageously, an alternating arrangement of riser and down pipes along the manifold is selected (for example, riser-down pipe-riser- . . . -down pipe-riser or riser-down pipe-riser-, . . . , -down pipe-riser-down pipe, or down pipe-riser-down pipe . . . -riser). Expediently, the positioning of inlets or outlets (for example, at the top or bottom end) in the photobioreactor according to this arrangement, is to naturally be chosen so that a dead volume is avoided. It is evident to a person skilled in the art that by reversing the flow of the culture medium, a riser can become a down pipe or vice versa. Advantageously, a flow velocity vector results from the sum of the flow velocity vectors of the flows of the culture medium prevailing in the manifold (in particular when a meandering flow is conducted in the reactor element), which flow velocity vector is substantially parallel to the longitudinal axis of the manifold (a net flow along the longitudinal axis, so to speak, see also the horizontal dashed arrows in FIG. 3).

To facilitate cleaning, the tube (in particular when it is formed as a manifold) and/or the risers or down pipes expediently comprise, optionally independently of each other, along their longitudinal axis, no bending of more than 90°, preferably more than 70°, more preferably more than 50°, even more preferably more than 30° or even more than 20°, in particular of more than 10° or even more than 5°. It is particularly favorable when the tube (in particular when it is formed as a manifold) and/or the risers or down pipes are substantially straight or straight along their longitudinal axis. Preferably, the tube (in particular when it is formed as a manifold) and/or the risers or down pipes (if necessary, except for any connection extensions) have a substantially round profile.

In a further, particularly preferred embodiment, the maintenance device is set up to clean the down pipe sealed by the maintenance device relative to the tube and the riser sealed by the maintenance device relative to the tube, both of which are connected in a liquid-permeable manner to each other by a connecting piece (that is, for example, can form a "U-tube"). Preferably, for this purpose, a cleaning instrument releasable by the maintenance device such as a sponge is released, pumped through said down pipe and said riser (which form, for example, a "U-tube") (also therefore, the maintenance device preferably having a pump, preferably a diaphragm pump) and expediently received again by the maintenance device (so that it is available again for the next release). In this way, portions of the reactor element can be cleaned more intensively, while the operation of the remaining part of the photobioreactor remains as undisturbed as possible.

It is favorable when the longitudinal axes of the risers or down pipes, optionally independently of each another, are at an angle of more than 5°, preferably more than 20°, more preferably more than 40° or even more than 60° more preferably more than 70° or even more than 80% in particular more than 85° or even more than 87.5° to the level of the culture medium or to the tube formed as a manifold. It is particularly favorable when the longitudinal axes of the risers or down pipes are substantially normal (or normal) to the level of the culture medium or to the (preferably substantially horizontal) manifold (in other words, when they are oriented vertically). Expediently, the longitudinal axes of the riser and down pipes (in particular of those which are each connected by a connecting piece) are substantially parallel to each other.

The photobioreactor of the present invention is preferably a type of tubular reactor, more specifically, a vertical tubular reactor, or not a plate reactor or flat panel reactor.

Especially with larger photobioreactors (which are equipped, for example, with a reactor element, having a long manifold to which dozens or hundreds of risers or down pipes are connected), the problem may arise that the maintenance device undesirably rotates over the length or represents a technical challenge in precisely controlling the maintenance device to the correct location in the tube (that is, for example, to precisely reach the correct U-tube). As a result, in a further preferred embodiment of the present invention, a guide bar for stabilizing and/or positioning the maintenance device in the tube is provided on the tube, preferably on the outside thereof. For example, the guide bar for stabilizing may be magnetic and the maintenance device may comprise a magnet (or vice versa). For positioning the maintenance device, the guide bar, for example, can comprise codings, for example, magnetic code carriers such as magnetic stripes or optical codes (for example, bar codes) at certain locations on the guide bar, which codings can be read by the maintenance device, whereupon, when the position to be reached is reached, the maintenance device is slown down (braked).

In a further preferred embodiment of the present invention, said drive system comprises at least one cable winch (preferably at least two cable winches at opposite ends of the tube) which can drive a cable guided in the tube and connected to the maintenance device. This has proven to be an efficient and robust drive for the maintenance device. The maintenance device can be supplied, for example, with power, compressed air or cleaning fluid (for example, via a high-pressure line) via lines in the cable or receive control signals. It is advantageous when the cable winch is equipped with a, in particular between cable winch and tube arranged, device for disinfecting the (possibly rolled therein) cable (for example, scraper for the cable at the cover outlet of the cable winch—spray nozzles with EtOH or disinfectant solution—scraper for cable after spraying). The cable, namely, when pulled out of the tube, is usually moist, and thus represents a possible nutrient medium for unwanted microorganisms (in particular when rolled up over a long time in the cable winch). These contaminating microorganisms can be introduced into the photobioreactor when the cable is pulled back into the tube from the cable winch (for example, when the maintenance device is pulled in the opposite direction by a second cable winch). A device for disinfecting the cable, however, at least largely avoids such contamination. In addition, or alternatively, the device for disinfection, for example, can comprise an ozone fumigation system for the winch room.

In order to reduce the risk of contamination through the cable (in addition or alternatively to that a device for disinfecting the cable is provided, for example as described above), it is provided, in another preferred embodiment that the cable guided in the tube and connected to the maintenance device is guided in the tube at least partially above the level of the culture medium (or at least partially in said gas space of the manifold). This reduces the contact of the cable with the culture medium.

In general, tubes for photobioreactors should be chemically resistant and not susceptible to deposition or residues or (UV-related) turbidity, which can reduce the light irradiation and thus reduce the yield. However, it has been found in the course of the present invention that it would be technically extremely complicated or even impossible to produce such tubes for photobioreactors with low manufacturing tolerance, in particular when they are substantially made of glass (which otherwise would have excellent properties for use in the photobioreactor). Consequently, there is a risk that a maintenance device, in particular when it exceeds a certain length (which, however, may be required to accommodate all desired functionalities in the maintenance device) and is rigid, gets stuck in the tube. Therefore, the maintenance device expediently comprises at least two modules ("wagons") which are connected to each another by a coupling, in order to reduce said risk and, as it were, to ensure a certain flexibility with regard to the manufacturing tolerance.

In order to further reduce the risk of contaminants depositing on the maintenance device (which, as explained above, represent a constant danger with respect to contamination of the culture), the photobioreactor according to an advantageous development of the invention comprises a station for the maintenance device, which station is set up for cleaning the maintenance device and/or for removing (or inserting) the maintenance device from the photobioreactor (or into the photobioreactor) and into which the maintenance device can be moved. Preferably, this station can be driven by the maintenance device directly from the tube. It is particularly preferred when this station, is equipped with at least one spray nozzle for cleaning the maintenance device, wherein the spray nozzle is preferably connected via a line to a liquid reservoir outside the tube.

In order to still further reduce the risk of contaminants depositing on the maintenance device, in a preferred embodiment of the present invention, the tube comprises a device for cleaning the maintenance device. This device preferably comprises at least one spray nozzle, in particular at least one annular arrangement of spray nozzles, through which the maintenance device can be moved for cleaning. Preferably, this spray nozzle or the spray nozzles of the arrangement is/are connected via a line to a liquid reservoir outside the tube.

The present invention typically allows for the use of (higher quality) glass components rather than disposable plastic components, among other things because the risk of glass breakage decreases when disassembly for cleaning is less often required. Thus, in a preferred embodiment of the photobioreactor, said tube and/or said risers and down pipes are made substantially of glass. As a result, among other things, the longevity or resistance of the photobioreactor is increased, in particular when microalgae are cultivated, which require a culture medium having an extreme pH value. In addition, glass typically roughens less with time than commonly used plastic, so that cleaning or keeping clean is simplified. The glass can be coated, as disclosed, for example, in DE 10 2009 029 792 A1 or WO 2011/015653 A2.

In a further preferred embodiment, the inner surface of the tube or the down pipes and risers, when present, is cleaned by the maintenance device at a pre-settable point in time, preferably wherein this process is repeated at least one further pre-settable point in time.

According to a further preferred embodiment, the maintenance device is set up to introduce one or more of the following into the culture medium in the tube (preferably at a pre-settable location in the tube optionally at a pre-settable point in time and/or depending on a sensor determined value (described in the following)): nutrients, excipients, further phototrophic microorganisms or further culture medium. Alternatively or additionally, in accordance with a further preferred embodiment of the photobioreactor according to the invention, the maintenance device comprises a sensor for determining a concentration of a substance in the culture medium (for example, a pH meter) or the microorganism concentration in the culture medium (for example, a photometer) or the temperature, preferably wherein the determination can be carried out at a pre-settable location in the tube optionally at a pre-settable point in time.

Usually, a part of the surface of the maintenance device, which surface is intended to come into contact with the culture medium, is made of plastic (for example, in the form of polyethylene tubes between modules of the maintenance device the outer surface of which comes into contact with the culture medium; see FIG. 5). Since it is preferred to cultivate phototrophic microorganisms for food production in the photobioreactor, it is expedient for reasons of food safety when this part does not exceed the total migration limit value of 10 mg/dm$^2$.

In a further aspect, the present invention provides a movable maintenance device for maintaining the inner surface of a tube of a photobioreactor for cultivating phototrophic microorganisms. This is suitable for the maintenance of the inner surface of the tube during ongoing operation of the photobioreactor, while liquid culture medium having the microorganisms at least partially flows through the tube, and is set up to be moved by an external drive system, which preferably comprises a cable winch, at least against the flow of culture medium in the tube. This also solves the problem mentioned in the introduction.

The movable maintenance device expediently comprises a connection part for connection to the external drive system. This is preferably a means for anchoring a cable (for example, an eyelet) in order to be able to be moved by a cable winch at least against the flow of the culture medium.

In a preferred embodiment, the movable maintenance device comprises a spray nozzle for spraying the inner surface of the tube with a cleaning fluid. This has proven as gentler and more hygienic compared to a brushing equipment in continuous operation. For supplying the spray nozzle with the cleaning liquid, the maintenance device comprises a connection for a line with the cleaning liquid, because for the reasons discussed above, the spraying of the culture medium with the microorganisms themselves can be disadvantageous.

In a further preferred embodiment, the movable maintenance device comprises at least one wiper blade made of an elastic material, such as a rubber, for wiping the inner surface of the tube. This has also proven as gentler and more hygienic compared to a brushing equipment in continuous operation. In this case, it is particularly preferred when the maintenance device is set up at least for wiping the inner surface of the tube with the wiper blade which inner surface is in contact with said gas space. In this way, deposits (which can arise over time as described above) can be better eliminated. Alternatively, or additionally, the maintenance device preferably comprises a, possibly further, spray nozzle, which is set up to spray the wiper blade with a cleaning liquid. This reduces the risk of dried residues forming on the wiper blade.

Furthermore, the maintenance device expediently comprises at least two modules ("wagons") which are connected to each other by a coupling in order to ensure, as it were, a certain flexibility with regard to the manufacturing tolerance of the tube.

In an advantageous development, the movable maintenance device is further equipped with a device for sealing of connections of the tube. This device preferably comprises an elastic seal (for example, an inflatable seal ring) having a cavity into which a fluid (for example, compressed air or said cleaning liquid) can be introduced under pressure to expand the seal and thereby seal the connection. The maintenance device preferably comprises a pump, in particular a diaphragm pump, for introducing the fluid into the cavity.

Usually, a part of the outer surface of the movable maintenance device is made of plastic (for example, in the form of polyethylene tubes between modules of the maintenance device the outer surface of which comes into contact with the culture medium, see FIG. 5). Since it is preferred to cultivate phototrophic microorganisms for food production in the photobioreactor, it is expedient for reasons of food safety when this part does not exceed the total migration limit of 10 mg/dm$^2$.

In a further aspect, the present invention relates to the use of the movable maintenance device just described for maintaining the inner surface of a photobioreactor tube for cultivating phototrophic microorganisms, wherein the maintenance takes place during ongoing operation of the photobioreactor, preferably while the culture medium is exposed to sunlight or artificial light; wherein liquid culture medium having the microorganisms at least partially flows through the tube.

"Operating state" herein is understood to mean a state of the photobioreactor in which live phototrophic microorganisms are cultivated in culture medium in the photobioreactor (in particular in the tube), wherein the culture medium in the photobioreactor (in particular in the tube) preferably comprises a flow.

The term "overall migration limit" is understood, to mean the maximum permissible quantity of non-volatile substances that are emitted from a material or article in food simulants. Preferably, this total migration limit is determined in accordance with Commission Regulation (EU) No. 10/2011 of 14 Jan. 2011 on plastic materials and articles intended to come into contact with foodstuffs, in the consolidated version of 26 Feb. 2015 (CELEX No. 02011R0010-20150226, hereinafter referred to as "the Regulation"), which already includes the following changes: amended by Commission Implementing Regulation (EU) No. 321/2011 of 1 Apr. 2011, Commission Regulation (EU) No. 1282/2011 of 28 Nov. 2011, Commission Regulation (EU) No. 1183/2012 of 30 Nov. 2012, Commission Regulation (EU) No. 202/2014 of 3 Mar. 2014, Commission Regulation (EU) No. 865/2014 of 8 Aug. 2014, Commission Regulation (EU) 2015/174 of 5 Feb. 2015; and corrected by rectification, Official Journal L 273 of 25 Oct. 2011, p. 13 (10/2011). In particular, in the context of the present invention, the standard test conditions "OM 2" are used according to Annex V, Chapter 3 of the Regulation, with a food simulant selected from food simulants A, B, C, D1 and D2 according to Annex III of the Regulation, preferably selected from A, B and C, even more preferably selected from A and B, in particular A.

The present invention further relates to the following embodiments:

Embodiment 1

A photobioreactor for cultivating phototrophic microorganisms, having a reactor element that comprises a tube, and having a maintenance device and a drive system that can move the maintenance device in the tube, wherein the photobioreactor is designed such that in the operating state of the photobioreactor, liquid culture medium having the microorganisms at least partially flows through the tube, characterized in that the photobioreactor is designed such that the maintenance device can be used in the operating state of the photobioreactor in the tube and can be moved by the drive system at least against the flow of the culture medium in the tube.

Embodiment 2

The photobioreactor according to embodiment 1, characterized in that the photobioreactor further comprises a device for gassing the culture medium, wherein the photobioreactor is designed such that in the operating state of the photobioreactor, the maintenance device in the tube is brought into contact with gas bubbles located in the culture medium.

Embodiment 3

The photobioreactor according to embodiment 1 or 2, characterized in that in the operating state of the photobioreactor, the culture medium can flow around and/or flow through the maintenance device in the tube.

Embodiment 4

The photobioreactor according to one of the embodiments 1 to 3, characterised in that the photobioreactor is designed such that both culture medium and, above the culture medium, a gas space for receiving gas bubbles rising from the culture medium, are present in the operating state in the tube, wherein in the tube, an interface is arranged between the culture medium and the gas space, and the maintenance device is set up at least for cleaning inner surface of the tube which inner surface is in contact with the gas space.

Embodiment 5

The photobioreactor according to one of embodiments 1 to 4, characterized in that the maintenance device comprises a spray nozzle for spraying the inner surface of the tube with a cleaning liquid, preferably wherein the maintenance device is set up at least for spraying inner surface of the tube by the spray nozzle which inner surface is in contact with said gas space.

Embodiment 6

The photobioreactor according to one of the embodiments 1 to 5, characterized in that the maintenance device comprises at least one wiper blade made of an elastic material for wiping the inner surface of the tube, preferably wherein the maintenance device is set up at least for wiping inner surface of the tube with the wiper blade which inner surface is in contact with said gas space and/or preferably wherein the maintenance device comprises an optionally further, spray nozzle, which is set up for spraying the wiper blade with a cleaning liquid.

Embodiment 7

The photobioreactor according to embodiment 5 or 6, wherein the spray nozzle is connected via a line to a liquid reservoir outside the tube.

Embodiment 8

The photobioreactor according to one of the embodiments 1 to 8, characterized in that the tube is a manifold having at least three connections for the inflow or outflow of culture medium, and the photobioreactor is designed such that the maintenance device can be moved to at least one of the connections in the tube and can seal the connection.

Embodiment 9

The photobioreactor according to embodiment 8, characterized in that the reactor element further comprises a plurality of risers and down pipes for the liquid culture medium, wherein the risers and down pipes are each connected in a liquid-permeable manner at their upper end to the tube formed as a manifold, wherein at least one of the risers and one of the down pipes are additionally connected in a liquid-permeable manner to each other by a connecting piece, and wherein the photobioreactor is designed such that the maintenance device at the same time can seal the down pipe connection and the riser connection, both of which are additionally connected to each other in a liquid-permeable manner by a connecting piece.

Embodiment 10

The photobioreactor according to embodiment 9, characterized in that the maintenance device is set up to clean the down tube sealed by the maintenance device relative to the tube and the riser sealed by the maintenance device relative to the tube, both of which are connected to each other in a liquid-permeable manner by a connecting piece.

Embodiment 11

The photobioreactor according to one of the embodiments 1 to 10, characterized in that on the tube, preferably on the outside, is provided a guide bar for stabilizing and/or positioning the maintenance device in the tube.

Embodiment 12

The photobioreactor according to one of the embodiments 1 to 11, characterized in that the drive system comprises at least one cable winch, which can drive a cable guided in the tube and connected to the maintenance device, preferably wherein the cable winch is equipped with a device for disinfecting the cable.

Embodiment 13

The photobioreactor according to one of the embodiments 1 to 12, characterized in that the maintenance device comprises at least two modules which are connected to each other by a coupling, preferably wherein the tube is made substantially of glass.

Embodiment 14

The photobioreactor according to one of the embodiments 1 to 13, characterised in that the photobioreactor comprises a station for the maintenance device, which is set up for cleaning the maintenance device and in which the maintenance device can be moved; and/or that the tube comprises a device for cleaning the maintenance device, preferably wherein this device comprises at least one spray nozzle, in particular at least one annular arrangement of spray nozzles through which the maintenance device can be moved for cleaning.

Embodiment 15

A method of cultivating phototrophic microorganisms in a photobioreactor, wherein the photobioreactor is equipped with a reactor element that comprises a tube and with a maintenance device in the tube and with a drive system that moves the maintenance device in the tube, wherein liquid culture medium having the microorganisms at least partially flows through the tube, characterized in that the method comprises the use of the maintenance device in the tube in the operating state of the photobioreactor and the maintenance device is moved by the drive system at least against the flow of the culture medium in the tube, preferably wherein the photobioreactor is further defined according to any of embodiments 1 to 14.

Embodiment 16

A movable maintenance device for the maintenance of the inner surface of a tube of a photobioreactor for the cultivation of phototrophic microorganisms, characterized in that the maintenance device is suitable for the maintenance of the inner surface of the tube in ongoing operation of the photobioreactor, while liquid culture medium having the microorganisms at least partially flows through the tube, and is set up to be moved by an external drive system, which preferably comprises a cable winch, at least against the flow of the culture medium in the tube.

Embodiment 17

The movable maintenance device according to Embodiment 16, characterized in that the maintenance device comprises a spray nozzle for spraying the inner surface of the tube with a cleaning liquid and a connection for a line with the liquid.

Embodiment 18

The movable maintenance device according to embodiment 16 or 17, characterized in that the maintenance device comprises at least one wiper blade made of an elastic material for wiping the inner surface of the tube, preferably wherein the maintenance device comprises a, possibly further, spray nozzle which is set up for spraying the wiper blade with a cleaning liquid.

Embodiment 19

The movable maintenance device according to one of the embodiments 16 to 18, characterized in that the maintenance device comprises at least two modules which are connected to each other by a coupling.

Embodiment 20

The movable maintenance device according to one of the embodiments 16 to 19, characterized in that the maintenance device is further equipped with device for sealing of connections of the tube.

Embodiment 21

A use of the movable maintenance device according to one of the embodiments 16 to 20 for maintaining the inner surface of a tube of a photobioreactor for cultivating phototrophic microorganisms, wherein maintenance takes place during ongoing operation of the photobioreactor, wherein liquid culture medium having the microorganisms at least partially flows through the tube.

Embodiment 22

The photobioreactor according to any of embodiments 1 to 14 or method according to embodiment 15, characterized in that a part of the surface of the maintenance device, which surface is intended to come into contact with the culture medium, is made of plastic, wherein the part has a total migration limit of at most 10 mg/dm$^2$.

Embodiment 23

The movable maintenance device according to one of the embodiments 16 to 20 or use according to embodiment 21, characterized in that a part of the outer surface of the maintenance device is made of plastic, wherein the part has a total migration limit of at most 10 mg/dm$^2$.

Embodiment 24

The photobioreactor according to one of the embodiments 1 to 14 or 22 or method according to embodiment 15 or 22, or movable maintenance device according to one of the embodiments 16 to 20 or 23 or use according to embodiment 21 or 23, characterized in that the maintenance device is designed such that while it is located in the tube, which has a first diameter, can clean with a cleaning instrument releasable from the maintenance device a further tube connected to the tube in a liquid-permeable manner at an angle (preferably between 40° and 140°, more preferably between 60° and 120°, more preferably between 80° and 100°, in particular substantially 90°), which further tube optionally has a diameter smaller or larger, preferably smaller, to the first diameter, optionally at the same time as the cleaning of the former tube.

Embodiment 25

The photobioreactor according to one of the embodiments 1 to 14 or 22 or 24 or method according to embodiment 15 or 22 or 24, or movable maintenance device according to one of the embodiments 16 to 20 or 23 or 24 or use according to embodiment 21 or 23 or 24, characterized in that the maintenance device has a weight of at least 0.5 kg, preferably at least 1 kg and/or a length of at least 0.5 m, preferably at least 1 m, and/or comprises a pump, preferably a diaphragm pump.

The invention is further elucidated on the basis of particularly preferred embodiments, to which, however, it is not limited, and with reference to drawings. The drawings show in detail:

FIG. 9 shows a plan view of an embodiment of the photobioreactor according to the invention in the operating state;

FIG. 10 is a locally enlarged view of the embodiment of FIG. 8 or FIG. 9;

FIG. 11A shows a plan view of a filled tube formed as a manifold as can be used for the present invention;

FIG. 11B is a perspective view of the tube according to FIG. 11A;

Figure 1:
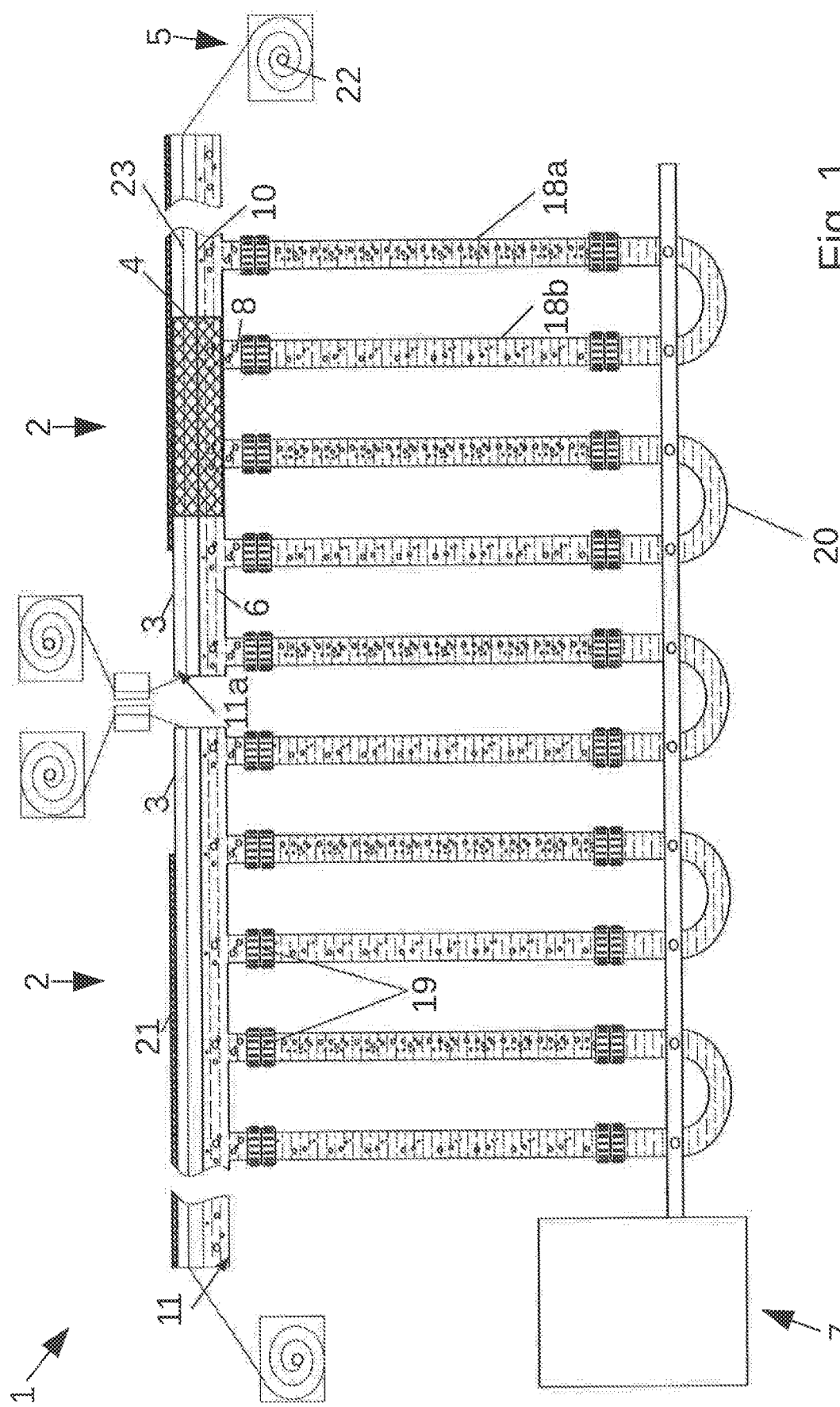
FIG. 1 shows a plan view of an embodiment of the photobioreactor according to the invention in the operating state.

FIG. 1 shows a photobioreactor 1 for cultivating phototrophic microorganisms, having two reactor elements 2, each comprising a plurality of vertical, straight risers 18a and down pipes 18b for culture medium 6 and a tube 3, which is horizontal, straight and formed as a manifold and further has a circular profile. The culture medium 6 is a liquid culture medium based on water and enriched with nutrients; it contains the phototrophic microorganisms (usually microalgae). The tube 3 and the risers or down pipes 18a or 18b are made of glass. The risers 18a and down pipes 18b are each connected in a liquid-permeable manner to the tube 3 formed as a manifold. The risers 18a and the down pipes 18b are additionally connected to each other in a liquid-permeable manner by a respective U-shaped connecting piece 20 (see also FIG. 10).

The maintenance device 4 is set up to clean the inner surface of the tube 3 by being equipped with spray nozzles and wiper blades for this surface. It comprises a magnet and is therefore stabilized in the tube 3 by the magnetic guide bar 21, which is attached to the outside of the tube 3. Consequently, the maintenance device is prevented from being able to rotate with respect to the longitudinal axis of the tube 3 when it is pulled through the tube 3 by the drive system 5 using the cables 23, which drive system 5 comprises cable winches. The guide bar 21 further comprises codings. These mark the locations in the tube 3, to which the individual risers or down pipes 18a or 18b are connected, and can be read by the maintenance device 4 and transmitted to a control system and processed by the latter.

The photobioreactor 1 further comprises a device 7 for gassing the culture medium 6 with carbon dioxide, wherein the gas is introduced into the risers 18a or the down pipes 18b. The culture medium 6 having the phototrophic microorganisms is so high in the reactor elements 2 that also the tubes 3 formed as manifolds are each at least 5%, preferably at least 10%, more preferably at least 20%, even more preferably at least 30% or even 40%, in particular half filled with it. Thus, both culture medium 6 and, above the culture medium 6, a gas space 9 for receiving gas bubbles 8 rising from the culture medium 6 are present in the tube 3, wherein an interface 10 between the culture medium 6 and the gas space 9 is arranged in the tube 3. Gas bubbles 8 gradually rising in the culture medium 6 due to their buoyancy come into contact with the maintenance device 4 and slow or prevent the deposition of residues to surfaces of the maintenance device 4.

The culture medium 6 (and the phototrophic microorganisms contained therein) can flow around the maintenance device 4 due to its shape, so that it can remain in the tube 3 during the entire operation of the photobioreactor 1. In continuous operation, it is pulled back and forth in the tube 3, in order to prevent, by its cleaning function, the laying down of contaminants in the tube 3 in early stages (in particular in the region of the inner surface of the tube 3, which is close to the interface 10, or in contact with it, and which region is particularly endangered in this regard). Two spray nozzles of the maintenance device 4 are oriented such that the maintenance device 4 is set up at least for cleaning inner surface 11a of the tube 3 which inner surface 11a is in contact with the gas space 9. Also, this inner surface 11a is particularly susceptible to contamination, because splashes of the culture medium 6 here dry easily and thus can leave residues such as dried microorganisms. Because the maintenance device 4 cannot rotate as described above due to the guide bar 21, it is ensured that the orientation of said spray nozzles is maintained in the direction of the surface 11a.

Figure 2:
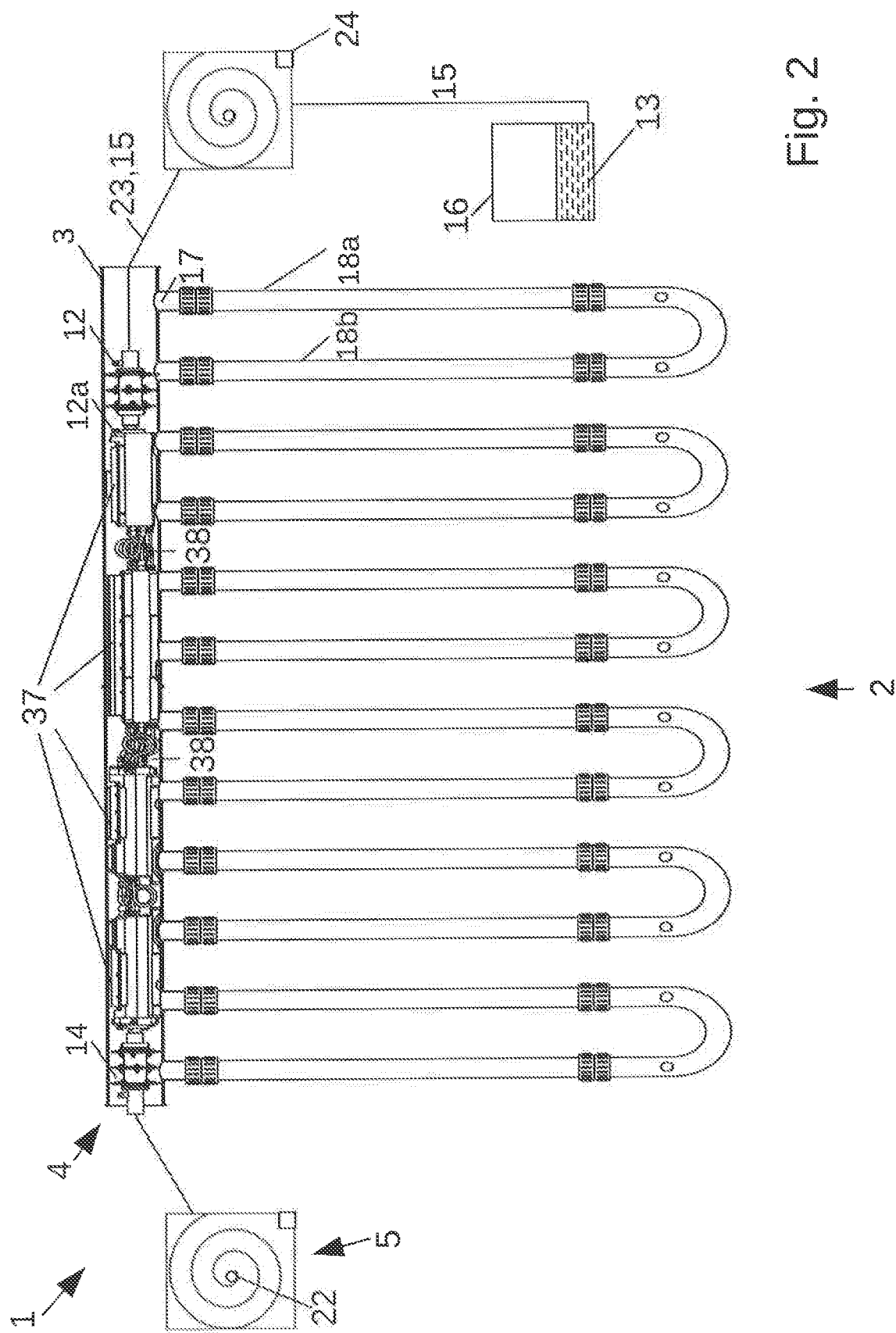
FIG. 2 shows a plan view of an embodiment of the photobioreactor according to the invention, in which the maintenance device is shown in more detail.

FIG. 2 shows a photobioreactor 1 for cultivating phototrophic microorganisms, having a reactor element 2 that comprises a plurality of vertical straight risers 18a and down pipes 18b for culture medium 6 and a tube 3 which is formed horizontally, straight and as a manifold. The culture medium 6 is a liquid culture medium based on water and enriched with nutrients; it contains the phototrophic microorganisms (usually microalgae). The risers 18a and down pipes 18b are each connected in a liquid-permeable manner to the tube 3 formed as a manifold.

The maintenance device 4 located in the tube 3 comprises four modules 37 which are connected to each other via couplings 38 to compensate for production-related angular misalignment of the tube 3, so that the maintenance device 4 cannot get stuck in the tube 3 when it is pulled through the tube 3 by the drive system 5 with the aid of the cable winches 22 functionally connected to the cable 23. The cable winches 22 are each equipped with devices 24 for disinfecting the cable 23, wherein these devices 24 are optionally configured as an ozone fumigation system.

The maintenance device 4 comprises the wiper blades 14 and the spray nozzles 12 for cleaning the inner surface of tube 3. The spray nozzles 12a serve to spray the wiper blades 14 to keep them moist. As a result, on the one hand, their cleaning effect is increased and on the other hand, deposits are prevented on the wiper blades themselves. The spray nozzles 12 or 12a are fed via a line 15 present in cable 23 from an external reservoir 16 with the cleaning liquid 13 (in this case, sterile water).

The maintenance device can be moved to each individual, interconnected pair of risers and down pipes 18a or 18b, respectively, and seal the tube 3 relative to them by blocking the respective connections 17. A pair of riser and down pipes 18a or 18b can thereby be exchanged (wherein the culture medium 6 is drained only from this part) without disturbing the operation in the remainder of the reactor element 2. Also, a rapid seal when there is broken glass in the pair is possible, wherein a leakage of the culture medium is significantly reduced. In this way, maintenance of the photobioreactor is substantially simplified, in particular in large breeding lines having dozens or hundreds of said pairs.

Figure 3:
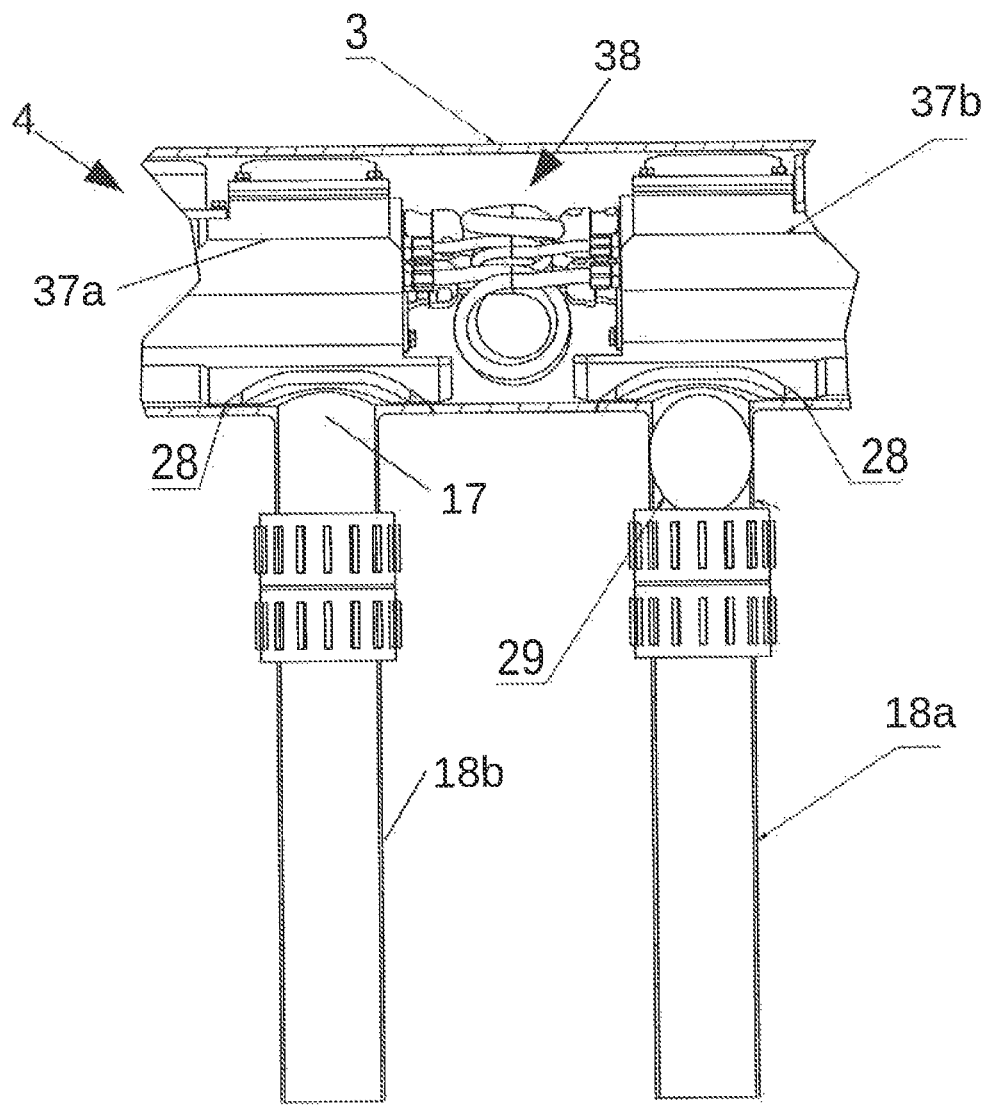
FIG. 3 is a locally enlarged view of the embodiment of FIG. 2, wherein the sealing and cleaning function of the maintenance device for an interconnected pair of riser and down pipe is shown.

FIG. 3 shows in detail the sealing and cleaning function of the maintenance device 4 for an interconnected pair of riser and down pipes 18a or 18b, which is connected to the tube 3 via the connections 17. The maintenance device 4 comprises two modules 37a and 37b, connected to each other via the coupling 38, substantially structurally identical, but oppositely oriented. The modules 37a or 37b are each equipped with a device 28 for sealing of connections of the tube 3. This device 28 is designed as a sealing ring into which gas (for example, air) or liquid (preferably fresh water from the external reservoir 16 to keep the interior of the sealing ring clean) can be introduced to expand the sealing ring and thereby to close the connection 17. If required (for example, due to damage), said pair of riser and down pipe 18a or 18b can now be replaced without disturbing the flow of the culture medium 6 in the tube 3.

In order to clean the pair of riser and down pipe 18*a* or 18*b*, a silicone-coated elastic ball 29 is pumped from a chamber in module 37*b* into riser 18*a*. By maintaining the pump pressure, the ball 29 passes through the entire riser 18*a*, the connecting piece to the down pipe 18*b*, and is received by a structurally identical chamber in module 37*a*, wherein deposits are removed from the inner walls of riser and down pipe and connecting piece. Thereafter, the maintenance device can be pulled to the next pair of riser and down pipe 18*a* or 18*b*, respectively, where the sealing and cleaning operation described is repeated (but in the reverse pumping direction, since the ball 29 is now located in the chamber of module 37*a*, alternatively, in the previous pair of riser and down pipe 18*a* or 18*b*, respectively, the ball 29 can be pumped back into the chamber of module 37*b* before the maintenance device is pulled to this next pair).

Figure 4:
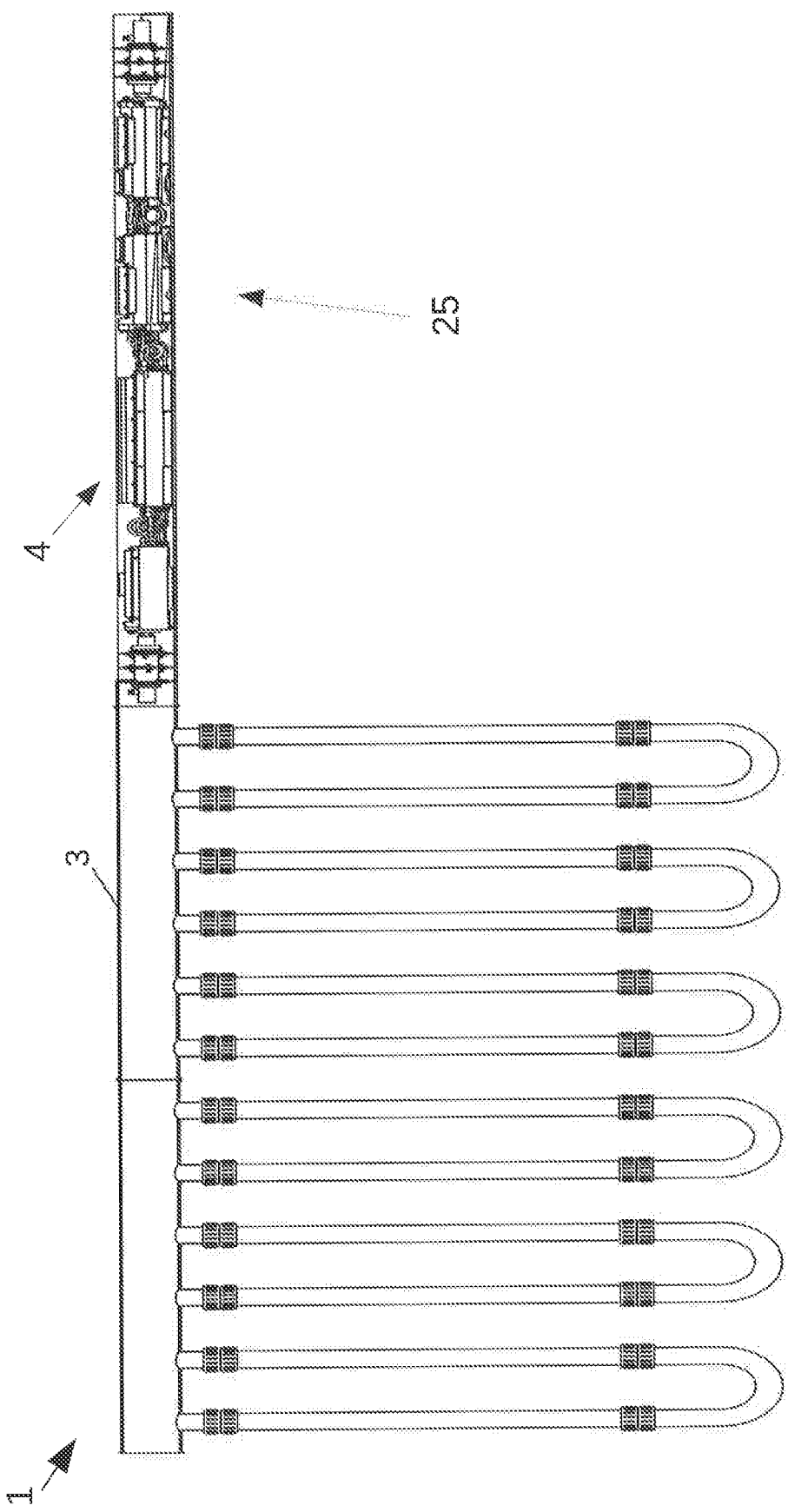
FIG. 4 shows schematically an embodiment of the photobioreactor according to the invention with the maintenance device in the station outside the tube.
Figure 5:
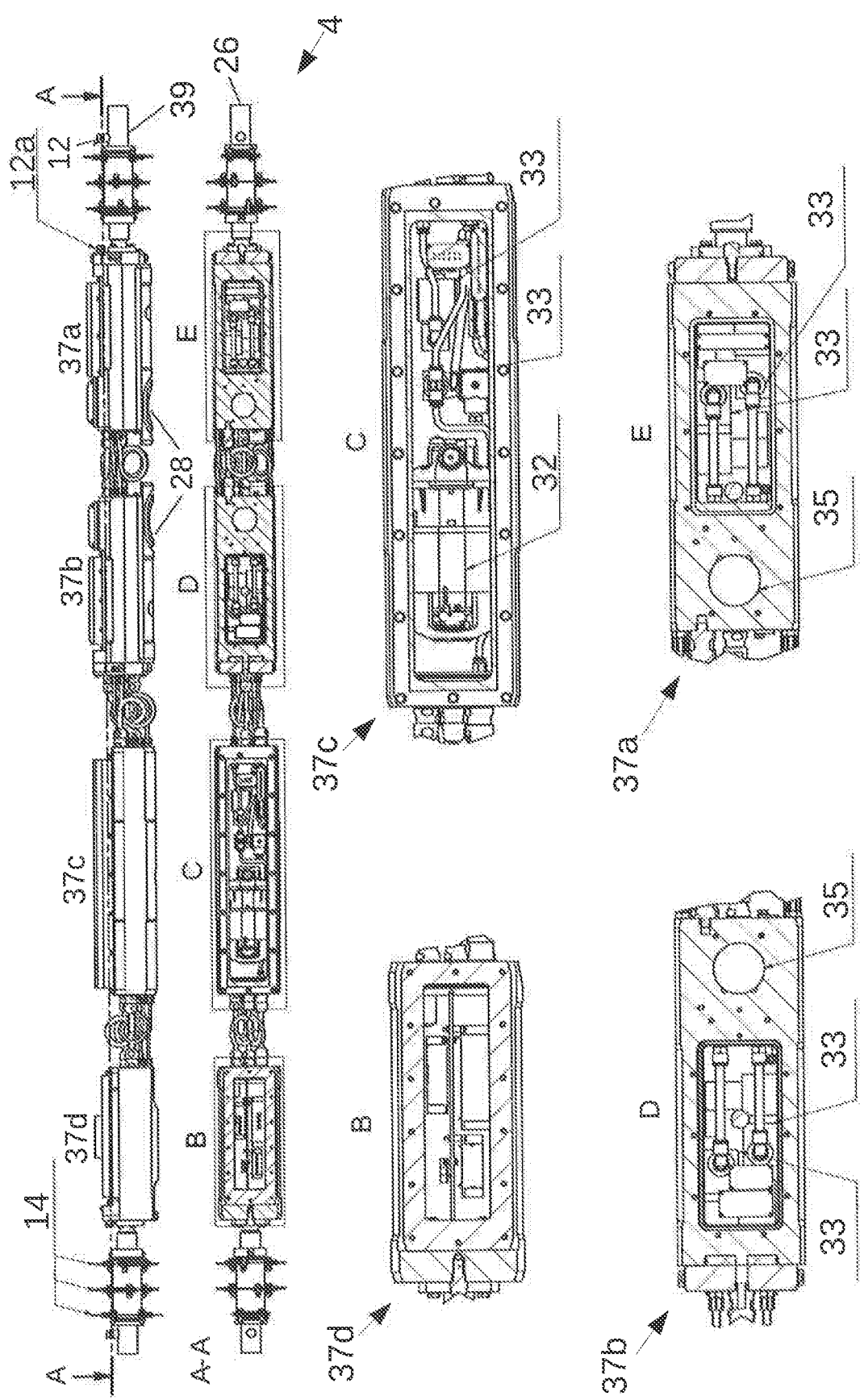
FIG. 5 shows different views of a preferred embodiment of the maintenance device according to the invention.

FIG. 4 schematically shows the photobioreactor 1 with the maintenance device 4 in the station 25, which can be driven directly out of the tube 3. This station 25 facilitates the removal or reinsertion of the maintenance device 4. The station 25 can have a higher level than the tube 3, so that the culture medium located therein does not flow into the station 25. When it is provided that the tube 3 is filled during operation, for example, only up to half the height, for example, it is also conceivable that the station 25 has the same level as the tube 3 (so to speak, an extension of the tube 3). Further, the station 25 has a sterile lid and a divisible lid, which ensures the possibility of removal of the maintenance device 4 and the lockability of the tube 3. FIG. 5 shows a preferred embodiment of the maintenance device 4 according to the invention, with the modules 37*a*-37*d*. Elements 39 are attached to the modules 37*a* and 37*d*, each element with three rows of wiper blades 14 made of silicone rubber. As can also be seen from FIGS. 6A and 6B, these three rows are rotatable with respect to each other and in each case do not cover the entire tube cross-section, so that the maintenance device 4 can be flowed around. In addition, a spray nozzle 12 for cleaning the inner surface of the photobioreactor tube is additionally provided on the modules 37*a* and 37*d*. The element 39 comprises a spray nozzle 12*a*, which is directed to the wiper blades 14. The distal end of element 33 serves to anchor the cable of the drive system 5 with cable winch 22. Since the line is provided with the cleaning liquid in the cable, the connection 26 for a line having the cleaning liquid is located at said end.

With this maintenance device 4, the entire cross-section of a photobioreactor tube (area in contact with the gas space above the culture medium—with any microorganisms deposited, area in contact with the interface between gas space and culture medium and area in contact with culture medium—with any biofilms) can simultaneously be cleaned when it is pulled through the tube.

The modules 37*a* and 37*b* are substantially structurally identical, but oriented in opposite directions. They are each equipped with magnetic valves 33 and a device 28 for sealing of connections of the tube. Connected to the device 28 is in each case the chamber 35, in which a releasable cleaning instrument 29, for example, a sponge, is stored, which can be pumped into further tubes connected to the tube. The module 37*c* includes a diaphragm pump 32 and further magnetic valves 33. Finally, module 37*d* houses the control electronics. Also illustrated with reference to FIG. 7 is that the culture medium can flow around all of the mentioned modules.

Figure 6A:
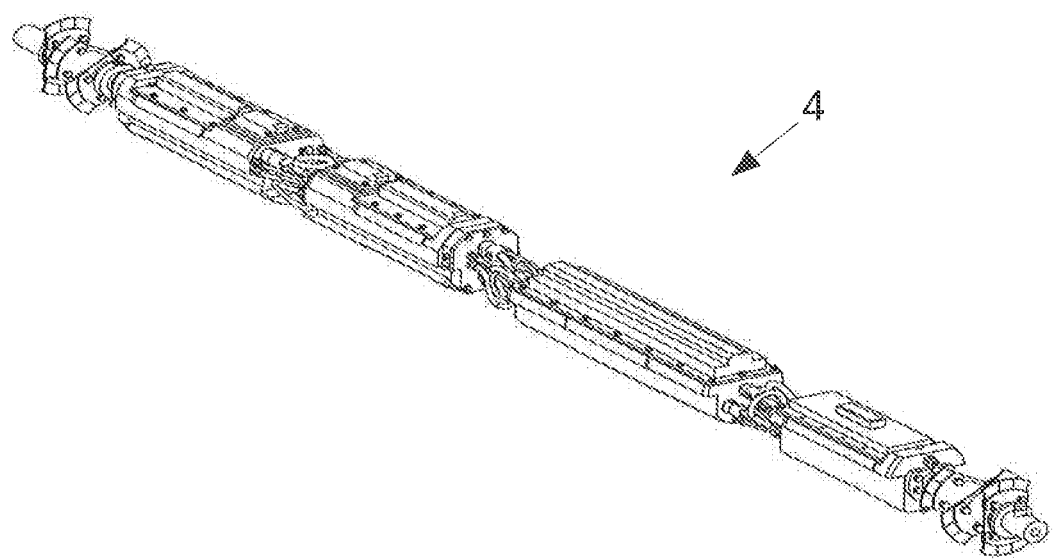
FIGS. 6a-6c show perspective views of a maintenance device according to FIG. 5.
Figure 6B:
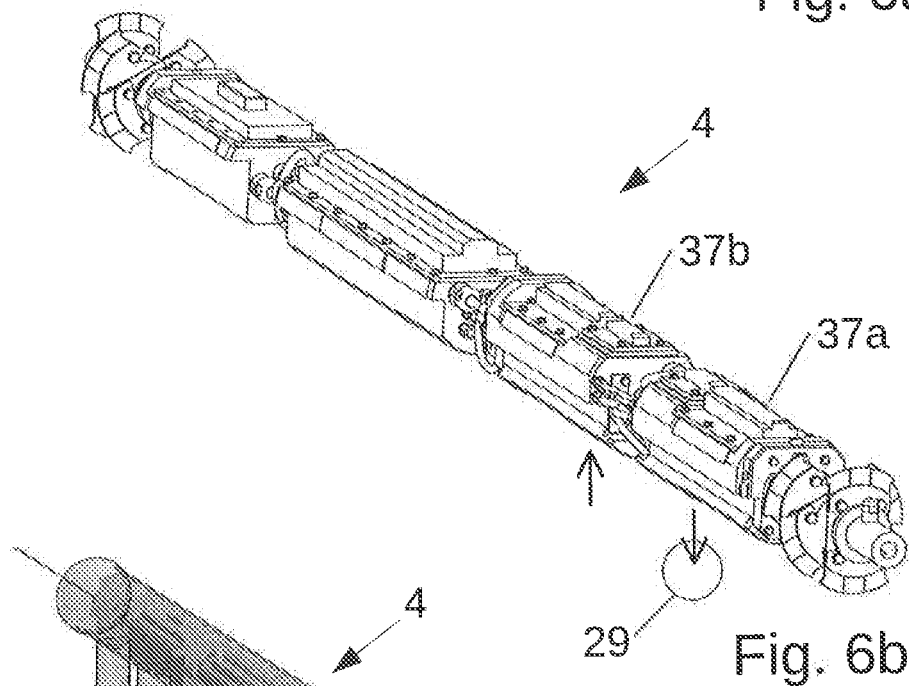
Figure 6C:
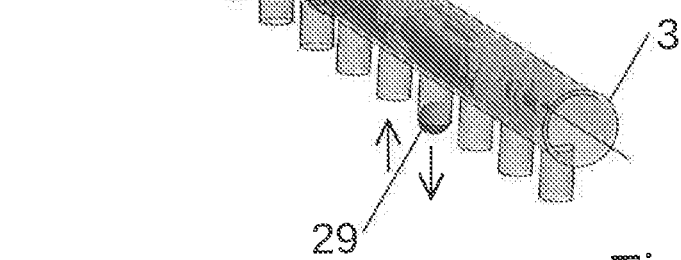

FIG. 6*a* shows a perspective view of the embodiment of the maintenance device 4 just described. FIG. 6*b* as well, wherein it is additionally illustrated, where the cleaning instrument 29 is released from the module 37*a* and is received again by the substantially structurally identical module 37*b*. FIG. 6*c* shows how this process takes place in the tube 3.

Figure 7:
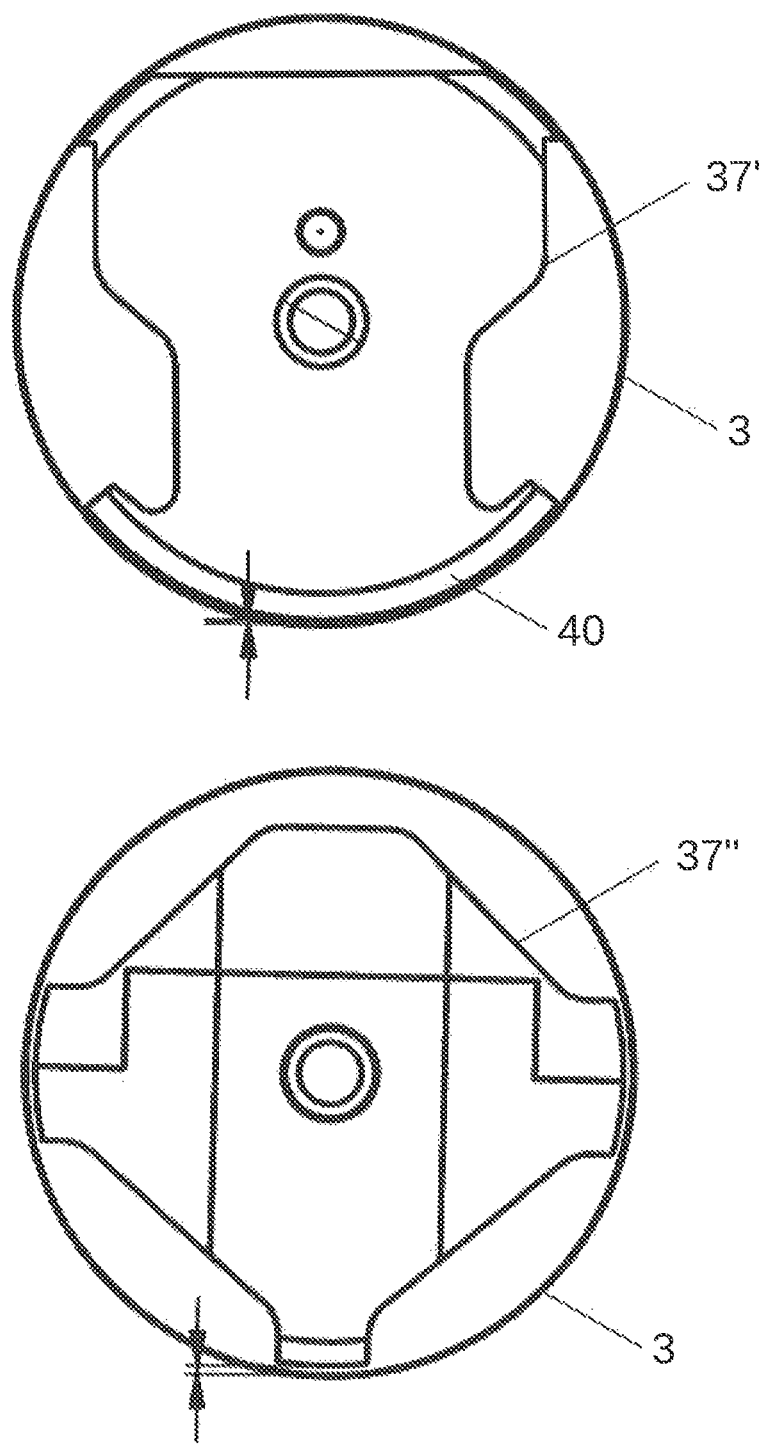
FIG. 7 shows, by way of example, cross-sections of modules of the maintenance device according to the invention in the tube, which ensure the ability to flow around.

FIG. 7 shows, by way of example, cross-sections of modules 37' or 37" of the maintenance device in the tube 3. Module 37' is in contact with tube 3 via a surface 40 of silicone rubber, which has an additional cleaning effect when the maintenance device moves. The cross-sections shown ensure that the culture medium having the microorganisms in the tube 3 can flow around the modules 37' or 37" substantially undisturbed.

Figure 8:
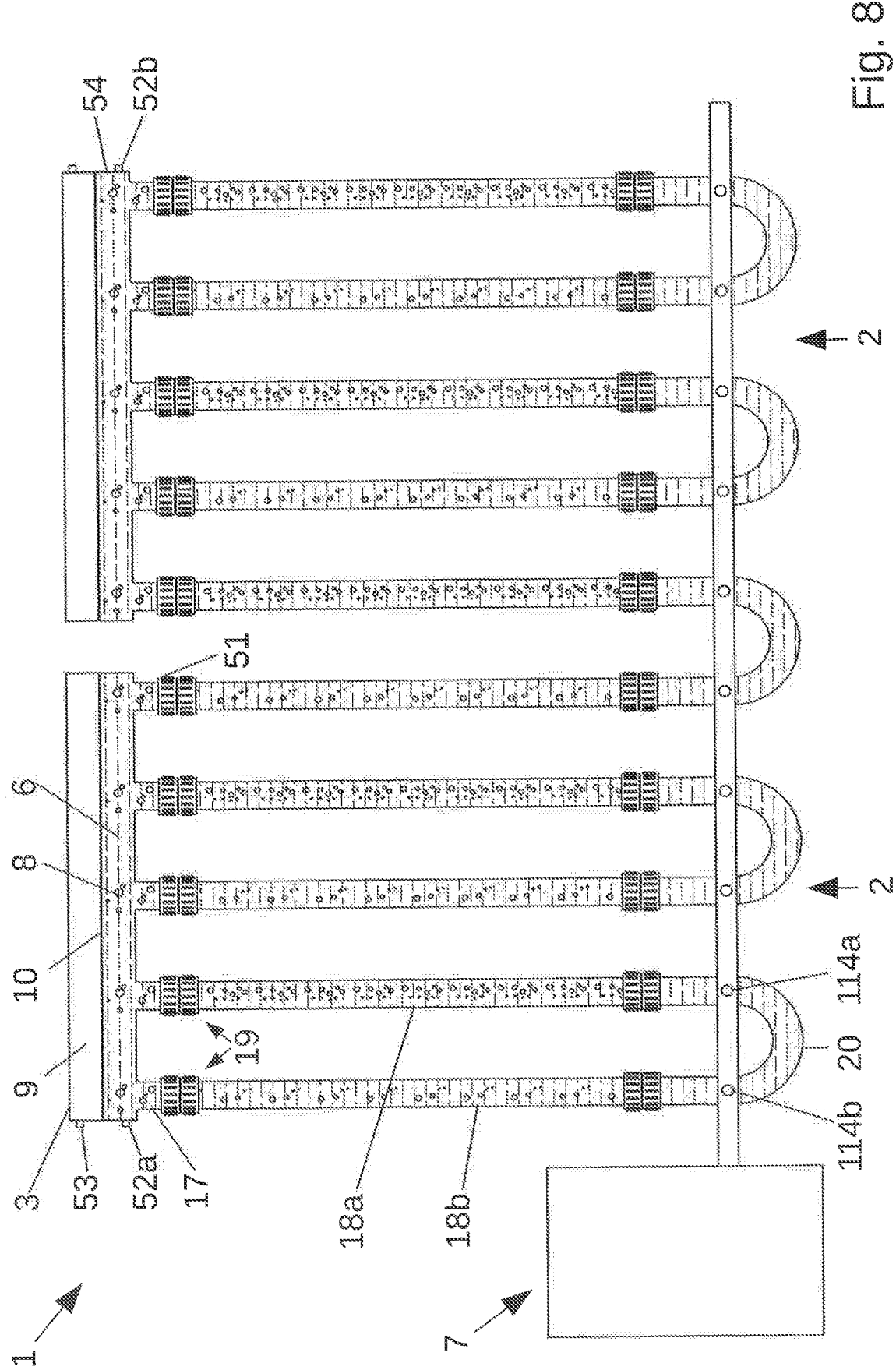
FIG. 8 is a plan view of an embodiment of the photobioreactor according to the invention in the operating state (maintenance device and drive system are not shown in this view)

The operation of particularly preferred embodiments of the photobioreactor according to the invention is further illustrated based on the following exemplary embodiments:

FIG. 8 shows a photobioreactor 1 for cultivating phototrophic microorganisms, having two reactor elements 2 each comprising a plurality of vertical straight risers 18*a* and down pipes 18*b* for culture medium 6 and a tube 3 which is formed horizontally, straight and as a manifold. The culture medium 6 is a liquid culture medium based on water and enriched with nutrients; it contains the phototrophic microorganisms (usually microalgae). The tube 3 and the risers or down pipes 18*a* or 18*b* are made of glass, wherein the tubes 3 are provided with connections 17 formed as connection extensions (see also FIGS. 11A and 11B). The risers 18*a* and down pipes 18*b* are each connected in a liquid-permeable manner at their upper end 19 with the aid of the tube connectors 51 to the connections 17 formed as connection extensions of the tube 3 formed as a manifold. The risers 18*a* and the down pipes 18*b* are additionally connected to each other in a liquid-permeable manner by a respective U-shaped connecting piece 20 (see also FIG. 10).

The photobioreactor 1 further comprises a device 7 for gassing the culture medium with a carbon dioxide-containing gas mixture ("gas"), wherein the gas is introduced into the risers 18*a* and the down pipes 18*b*. An inlet 114*a* for gassing by the device 7 is provided for the riser 18*a* connected to the down pipe 18*b* through the connecting piece 20. A further inlet 114*b* is provided for gassing by the device 7 for the down pipe 18*b* connected to the riser 18*a* through the connecting piece 20. The carbon dioxide is introduced from a liquid tank into a gas manifold. The connections of the gas manifold are connected by hoses to one inlet 114*a* and 114*b*, respectively. By providing an opening of the inlet 114*a*, which is more permeable than the opening of the inlet 114*b*, or by different gas pressures in 2 gas manifolds separate from each other, a greater gassing of the risers 18*a* relative to the down pipes 18*b* is made possible. As a result, although no U-shaped connecting pieces 20 are provided at the respective upper end 20 of the risers 18*a* or down pipes 18, but the tube 3 formed as a manifold is provided, a meandering flow of the culture medium 6 is created (upwards in the risers 18*a*, downward into the down pipes 18*b*, see also the dashed arrows in FIG. 9). This meandering flow is additionally stabilized further in that the two reactor elements 2 are connected to each other in a liquid-permeable manner through a U-shaped connecting piece 20 via a down pipe 18*b* of the first reactor element 2 with a riser 18*b* of the second reactor element 2, that is, in simplified terms, by providing a "gap" between the two tubes 3 formed as manifolds.

The inlet 52*a* and the outlet 52*b* can be connected to each other, thereby allowing cyclical operation of the photobioreactor 1. After a certain number of cycles under exposure with light, the culture medium 6, which now contains a significantly higher concentration of microorganisms, can be removed at the outlet 52b for harvesting (that is, for concentration and drying of the phototrophic microorganisms), while fresh culture medium 6 having a low initial concentration of phototrophic microorganisms is introduced at the inlet 52a. Of course, a continuous cyclic operation is also conceivable in which the inlet 52a remains connected to the outlet 52b by a hose, and fresh culture medium 6 is continuously supplied at an inlet in a first lower connecting piece 20 and the same amount of denser culture medium 6 is continuously removed at an outlet in a second lower connecting piece 20 which lies directly in front of the connection piece 20 seen in the flow direction. This naturally requires a certain minimum length of the breeding line. Also, when the photobioreactor 1 has a certain minimum length, a continuous linear operation is also conceivable in which fresh culture medium 6 having a low initial concentration of phototrophic microorganisms is continuously introduced at the inlet 52a and the same amount of mature culture medium 6 is continuously removed at the outlet 52b for harvesting. However, inlets can also be provided at other locations of the reactor (for example, U-bend connecting piece 20 of the first/last riser or down pipe 18a or 18b, but also in another U-bend connecting piece 20 in the photobioreactor).

The meandering flowing culture medium 6 having the phototrophic microorganisms is so high in the reactor elements 2 that the tubes 3, which are formed as manifolds, are each filled about halfway therewith. Thus, both culture medium 6 and, above the culture medium 6, a gas space 9 for receiving gas bubbles 8 rising from the culture medium 6 are present in the tube 3, wherein an interface 10 is arranged between the culture medium 6 and the gas space 9 in the tube 3. The gas pressure equalization with the environment takes place via an opening 53 which is equipped with a filter system in order to avoid contamination of the culture medium 6.

The contaminants on the inner surface of the tube 3 associated with the interface 10 between the culture medium 6 and the gas space 9 could be compared with the prior art (which does not provide the interface in a manifold, but at much more difficult to reach locations; see, for example, US 2011/0027875 A1, in particular the lower part of FIG. 1 therein) cleaned with relatively little effort in which the photobioreactor 1 is briefly taken out of service, the culture medium 6 is discharged from the tube 3, the cover plate 54 of the tube 3 is removed and the inner surface of the tube 3, for example, is cleaned with a brush attached to a telescopic rod. However, the use of the maintenance device 4 provided according to the invention leads to much better results, as also described in the following.

The maintenance device 4 in the photobioreactor 1 shown in FIG. 9 enables the cleaning or keeping clean of the inner surface of the tube 3 formed as a manifold during operation. In this case, the guide bar 21 for the maintenance device 4 is provided on the tube 3. The maintenance device 13 is equipped with a spray nozzle 12 for spraying the inner surface of the tube 3. The maintenance device 4 has a magnetic element and can be positioned against rotation by the guide bar 21. The maintenance device 4 can be flowed around (so that the meandering flow of the culture medium 6 is not significantly disturbed) and can be used at presettable time intervals during ongoing operation, which substantially reduces the idle times of the photobioreactor 1. The maintenance device 4 can remain in the tube 3, even when it is not currently used. The dashed arrows illustrate the flow path in the reactor element 2.

Figure 12:
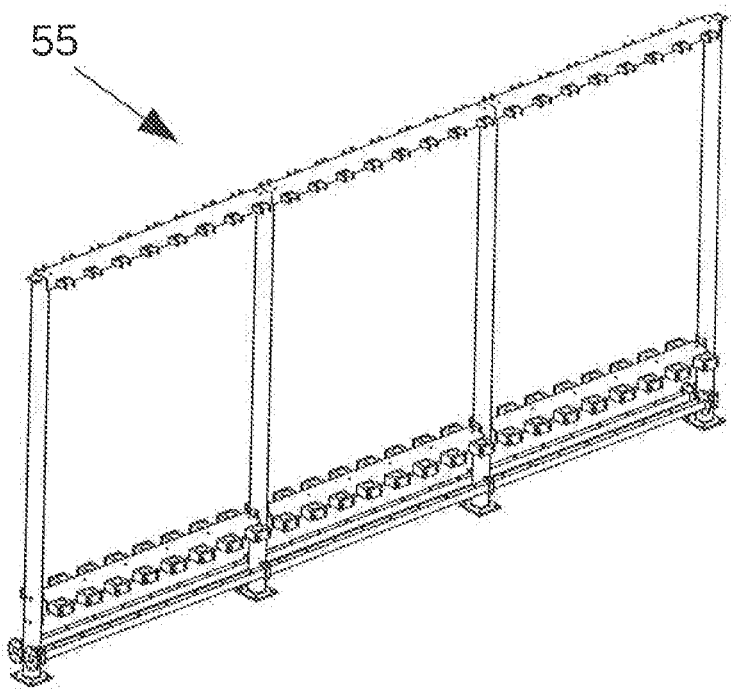
FIG. 12 shows a perspective view of a metal framework, as can be for embodiments of reactor elements of the photobioreactor according to the invention.
Figure 13:
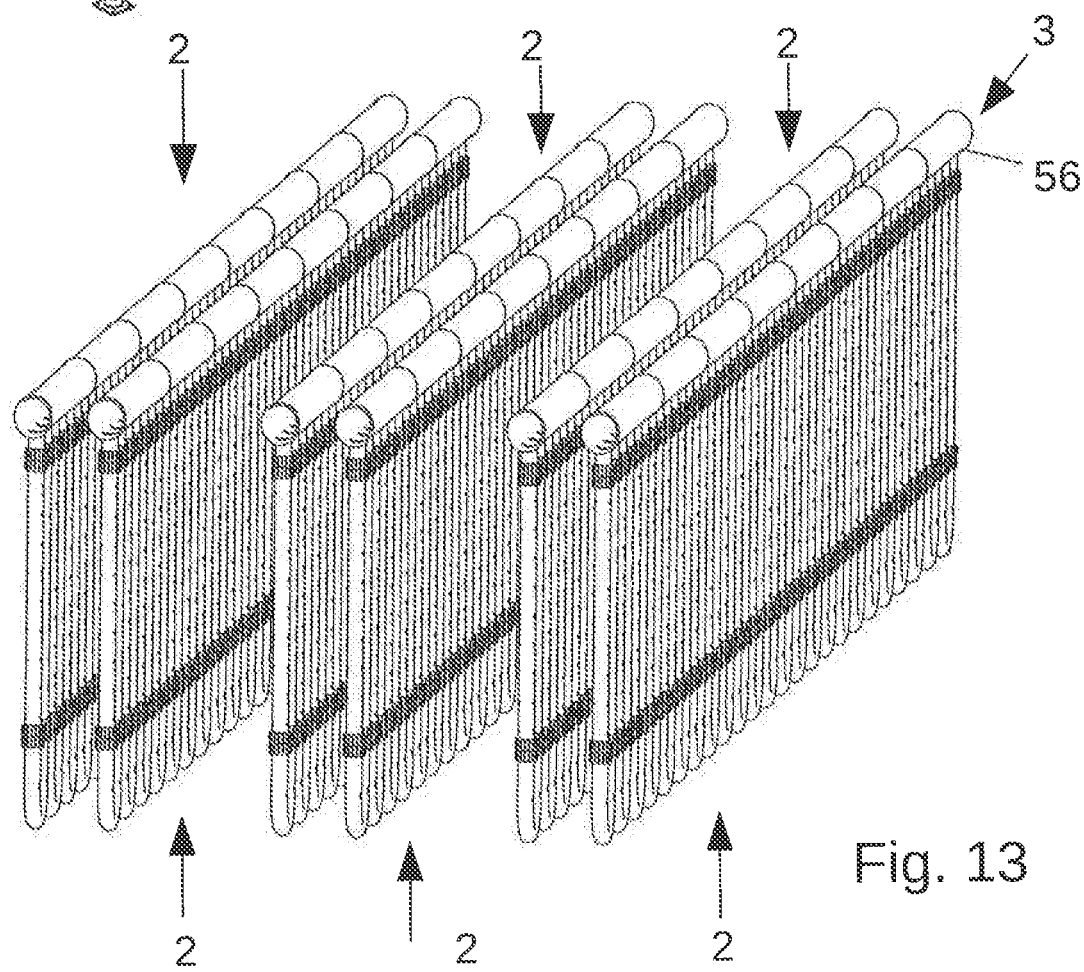
FIG. 13 shows a perspective view of reactor elements of one embodiment of the photobioreactor according to the invention.

FIG. 13 schematically shows an embodiment of the photobioreactor 1 in which the respective tube 3 of a reactor element 2 formed as a manifold is made of glass parts 56 which are directly connected to each other. In each case, two reactor elements 2 are held by the metal frame 55 shown in FIG. 12.

The invention claimed is:

1. A photobioreactor for the cultivation of phototrophic microorganisms, comprising:
   a) a reactor element that comprises a tube;
   b) a maintenance device that is located in the tube;
   c) a drive system configured to move the maintenance device in the tube, and
   d) a passing device for gassing a culture medium in which the phototrophic microorganisms are cultivated;
   wherein in an operating state of the photobioreactor, a liquid culture medium comprising the phototrophic microorganisms at least partially flows through the tube and wherein, in the operating state of the photobioreactor, the maintenance device is movable by the drive system at least against a flow of the liquid culture medium in the tube.

2. The photobioreactor according to claim 1, wherein, in the operating state of the photobioreactor, the maintenance device is brought into contact with gas bubbles located in the culture medium in the tube.

3. The photobioreactor according to claim 1, wherein, in the operating state of the photobioreactor, the liquid culture medium and a gas space for receiving gas bubbles rising from the liquid culture medium are present in the tube,
   wherein an interface is formed between the liquid culture medium and the gas space in the tube, and
   wherein the maintenance device is set up at least for cleaning an inner surface of the tube that is in contact with the gas space.

4. The photobioreactor according to claim 1, wherein the maintenance device comprises a spray nozzle for spraying the inner surface of the tube with a cleaning liquid.

5. The photobioreactor according to claim 4, wherein the spray nozzle is connected via a line to a liquid reservoir outside the tube.

6. The photobioreactor according to claim 1, wherein the tube is a manifold having at least three connections for the inflow or outflow of the liquid culture medium, and
   wherein the maintenance device is moveable to at least one of the connections in the tube to seal the connection.

7. The photobioreactor according to claim 6, wherein the reactor element further comprises a plurality of risers and down pipes for the liquid culture medium,
   wherein the risers and down pipes are each connected in a liquid-permeable manner at their upper end to the tube formed as a manifold,
   wherein at least: one of the risers and one of the down pipes are additionally connected to each other in a liquid-permeable manner by a connecting piece, and
   wherein the maintenance device is configured to seal the connection for the down pipe and the connection for the riser, which are connected to each other in a liquid-permeable manner by the connecting piece.

8. The photobioreactor according to claim 7, wherein the maintenance device is set up to clean the down pipe sealed by the maintenance device relative to the tube and the riser sealed by the maintenance device relative to the tube, wherein the down pipe and riser to be cleaned are connected to each other in a liquid-permeable manner by the connecting piece.

9. The photobioreactor according to claim 1, wherein the drive system comprises at least one cable winch, which drives a cable guided in the tube that is connected to the maintenance device.

10. A method for cultivating phototrophic microorganisms in the photobioreactor of claim 1, the method comprising:
   a) flowing the culture medium comprising the phototrophic microorganisms through the tube under conditions in which the phototrophic microorganisms grow; and
   b) moving, via the drive system, the maintenance device in the tube in the operating state of the photobioreactor at least against the flow of the culture medium in the tube, whereby light transmission into the tube is maintained.

11. The photobioreactor according to claim 3, wherein the maintenance device comprises a spray nozzle for spraying a cleaning fluid, and wherein the maintenance device is set up at least for spraying the inner surface of the tube in contact with the gas space with the spray nozzle.

12. The photobioreactor according to claim 9, wherein the cable winch is equipped with a disinfecting device for disinfecting the cable.

13. A method for cultivating phototrophic microorganisms in the photobioreactor according to claim 11, the method comprising:
   a) flowing the culture medium comprising the phototrophic microorganisms through the tube under conditions in which the phototrophic microorganisms grow; and
   b) moving, via the drive system, the maintenance device in the tube in the operating state of the photobioreactor at least against the flow of the culture medium in the tube; and
   c) cleaning with the maintenance device at least the inner surface of the tube that is in contact with the gas space by spraying through the spray nozzle at least said inner surface with the cleaning liquid in the operating state of the photobioreactor.

14. The method according to claim 13, wherein the driving system comprises a cable winch.

* * * * *